United States Patent [19]

Rosenberg et al.

[11] 4,338,320

[45] Jul. 6, 1982

[54] ESTERS OF 6'-HYDROXYCINCHONINE, AND A METHOD OF TREATING ARRYTHMIA WITH THEM

[75] Inventors: Harry Rosenberg, Omaha; LaVerne D. Small, Lincoln, both of Nebr.

[73] Assignee: The Board of Regents of the University of Nebraska, Nebr.

[21] Appl. No.: 960,934

[22] Filed: Nov. 15, 1978

[51] Int. Cl.³ ..................... A61K 31/49; C07D 453/04
[52] U.S. Cl. .................................... 424/259; 546/134; 542/427
[58] Field of Search ........................ 546/134; 424/259; 542/427

[56] References Cited

U.S. PATENT DOCUMENTS

| | | | |
|---|---|---|---|
| 2,033,515 | 3/1936 | Cretcher et al. | 546/134 |
| 2,033,555 | 3/1936 | Souther et al. | 546/134 |
| 2,033,679 | 3/1936 | Butler et al. | 546/134 |
| 3,663,552 | 5/1972 | Yardley et al. | 546/134 |
| 3,819,635 | 6/1974 | Pachter et al. | 546/74 |
| 3,823,146 | 7/1974 | Grethe et al. | 546/134 |
| 3,857,837 | 12/1974 | Gutzwiller et al. | 546/134 X |
| 4,017,497 | 4/1977 | Lim et al. | 546/74 |

OTHER PUBLICATIONS

Dega–Szafran, Bull. Acad. Pol. Si., Ser. Sci. Chim., 14(8), pp. 529–534 (1966) Chemical Abstracts, vol. 66, 38,088k (1967).
Prajer, et al., Roczniki Chem. 26, pp. 555–564 (1952).
McOmie, et al., Chemical Abstracts, 59, 15202h (1963).
Henry, et al., J. Chem. Soc., 1934, pp. 1923–1929.
Rice, J. Med. Chem., vol. 20, No. 1, pp. 164–165 (01/77).
Liebman, et al., J. Org. Chem., vol. 43, No. 4, pp. 737–739 (04/78).
Iijima, et al., J. Med. Chem., vol. 21, No. 4, pp. 398–400 (04/78).
McOmie, et al., Tetrahedron, vol. 24, pp. 2289–2292 (1968).

*Primary Examiner*—Donald G. Daus
*Assistant Examiner*—Diana G. Rivers
*Attorney, Agent, or Firm*—Kokjer, Kircher, Bradley, Wharton, Bowman & Johnson

[57] ABSTRACT

The novel compound cupreidine is the subject of the present invention. The invention also encompasses a method of synthesizing cupreidine utilizing boron tribromide to achieve demethylation of the starting compound quinidine. The novel compound cupreidine has been shown to be effective in the treatment of cardiac arrhythmia in warm blooded animals.

2 Claims, No Drawings

ESTERS OF 6'-HYDROXYCINCHONINE, AND A METHOD OF TREATING ARRYTHMIA WITH THEM

FIELD OF THE INVENTION

This invention relates generally to cinchona alkaloid compounds and, more particularly, to a novel substituted alkaloid, cupreidine, its synthesis and use.

BACKGROUND

Substituted cinchona alkaloids have long been known for their profound physiological activity. For example, U.S. Pat. No. 3,663,552 discloses substituted quinine, quinidine, cinchonine and cinchonidine for use as antimalarial and antiarrhythmic compounds. An improved method of preparing these compounds is disclosed in U.S. Pat. No. 3,823,146.

Cupreidine is mentioned as a theoretical compound in U.S. Pat. No. 2,033,679 filed Feb. 27, 1934. The patentees do not disclose or claim to have synthesized the compound, however. In 1933 Ludwiczakowna et al. claimed the synthesis of cupreidine by demethylation through treating with sulfuric acid. 52 *Rec. Trav. Chim.* p. 847 (1933). It was later proven that the demethylation reaction carried out by Ludwiczakowna et al. does not yield cupreidine but, instead, dihydrocupreidine. Henry and Solomon, *J. Chem. Soc.*, 1934, p. 1924.

Quinidine has remained one of the most important and efficacious drugs for maintaining normal heart rhythm notwithstanding significant side effects associated with its use. Quinidine has two structural groups that are potentially reactive. Thus, efforts have been made to synthesize quinidine derivatives which would have useful therapeutic activity with a lower level of toxicity than quinidine. These efforts have met with very limited success.

OBJECTS OF THE INVENTION

It is, therefore, a primary object of the present invention to synthesize quinidine derivatives which will exhibit antiarrhythmic activity.

As a corollary to the above object, it is a principal aim of the invention to synthesize cupreidine and analogs of cupreidine.

Another objective of the invention is a method of treating arrhythmia by utilzing quinidine derivatives.

As a corollary to the foregoing, an important object is to provide a method of treating arrhythmia utilizing cupreidine and analogs of cupreidine.

A further object of this invention is to provide a novel method of synthesizing cupreidine and analogs thereof which will produce acceptable yields utilizing available starting reagents.

Other objects and aims will be made clear or become apparent from the following description and claims.

DESCRIPTION OF THE PREFERRED EMBODIMENT

Dried quinidine base is dissolved in a suitable anhydrous solvent, preferably methylene chloride. The solution is then cooled to below room temperature, preferably in the range of −65° to −75° C. Four molar equivalents of boron tribromide are added per mole of quinidine. The reaction is substantially instantaneous and the product may be isolated using conventional extraction techniques.

To improve yield, the post reaction mixture may be allowed to rise slowly in temperature to the range of room temperature to about 40° C. with refluxing for about one hour. The refluxed product is cooled to 0° to 5° C. and then vigorously stirred while equal quantities of ice water and 10% NaOH are added, stepwise. This addition will dissolve the precipitate and permit separation of the aqueous phase from the methylene chloride.

The aqueous phase is filtered, acidified to pH 2 by the addition of Hcl and then basified to pH 9 with $NH_4OH$. Final extraction is with chloroform or butanol.

The structure of the reaction product obtained through the foregoing process has been confirmed as cupreidine through NMR and mass spectroscopy. It is thought that the reaction proceeds via the following intermediates:

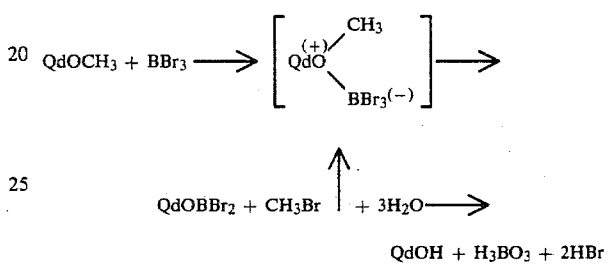

UTILITY OF THE PREFERRED EMBODIMENT

The compound cupreidine synthesized according to the technique discussed above has been found to have an effectiveness equal or superior to quinidine as an antiarrhythmic agent.

Mice were treated at varying dosage levels for both quinidine and cupreidine. A dose probit curve was generated for the effective dose and lethal dose of each compound. The respective $ED_{50}$ and $LD_{50}$ values were derived from those curves using techniques well known to those skilled in the art. The results are summarized below:

TABLE I

|  | Quinidine | Cupreidine |
| --- | --- | --- |
| $ED_{50}$ (mg/kg) | 22.4 | 23.5 |
| $LD_{50}$ (mg/kg) | 202 | 304 |

An effective dosage of cupreidine, within the range of about 20.6 to about 26.8 mg/kg was administered intraperitoneally to mice and an effective dosage of quinidine 19.5–25.8 mg/kg was likewise administered to another group. Aconitine was used to induce arrhythmia and a saline solution served as the control for a third group. The results are summarized in the following table:

TABLE II

|  | Saline | Quinidine | Cupreidine |
| --- | --- | --- | --- |
| Onset of Arrhythmia (time in seconds) | 153. ± 5 | 194. ± 11 | 198. ± 8 |
| Onset of Ventricular Tachycardia (time in seconds) | 193. ± 11 | 294. ± 44 | 250. ± 22 |

The compound of the present invention may be administered intravenously, orally or intraperitoneally depending upon the subject and the particular arrhythmia being treated. A number of physiologically acceptable carriers may be employed, the selection of one of which is well within the skill of the art. Both liquid and solid carriers are available depending upon the desired method of administration. It will also be appreciated that the treatment program including dosage and frequency is comparable to quinidine and quinidine derivatives and, therefore, within the skill of the art. From the foregoing it will be appreciated that the efficacy of the compound which is the subject of this invention, namely cupreidine, is comparable to that of quinidine with greatly reduced toxicity.

ALTERNATIVE EMBODIMENTS OF THE INVENTION

The following examples illustrate the synthesis of a number of analogs of cupreidine which are within the scope of the present invention:

Example 1

Ethylcupreidine (6-Ethoxycinchonine)

Anhydrous potassium carbonate (1.5 g) and one equivalent (0.5 ml) ethyl iodide were added to 1.9 g cupreidine dissolved in 250 ml of 2-butanone. The mixture was stirred under nitrogen and warmed for 3 hours at 60° C. The solvent was then evaporated and replaced by chloroform and water. After several minutes of shaking, the chloroform layer was removed, washed with dilute sodium hydroxide solution, dried, and evaporated to yield crude ethyl cupreidine. The product was crystallized from a mixture of acetone, ethyl alcohol and water. Mass spectroscopy was used to characterize the product as 6'-ethoxycinchonine.

Example 2

Benzylcupreidine (6'-Benzyloxycinchonine)

The potassium salt of cupreidine was prepared by dissolving cupreidine in a small amount of methanol followed by the addition of one equivalent of potassium hydroxide. After stirring for a short time, the alcohol was evaporated yielding a yellow crystalline solid that was dried in a vacuum oven at 30 inches of mercury vacuum and 40° C. for 20 hours. The dry potassium 6'-oxycinchonine (4 g) was dissolved in 950 ml of dry 1,2-dimethoxyethane (monoglyme). After the reaction flask was thoroughly flushed with dry nitrogen, one equivalent of tetrabutylammonium chloride was added and the mixture was then stirred for several hours. Slightly less than one equivalent of benzyl bromide was added to the reaction mixture which was subsequently stirred for 15 hours and then concentrated, and cooled. This was followed by the addition of 250 ml of cold 5% aqueous sodium hydroxide to induce the precipitation of 6'-benzyloxycinchonine which was removed by filtration and washed several times with cold 5% aqueous sodium hydroxide to remove unreacted cupreidine. After recrystallization, mass spectroscopy was utilized to characterize this product as 6'-benzylcupreidine.

Example 3

Allylcupreidine (6'-Allyloxycinchonine)

This compound was prepared by the same procedure set forth in Example 2 above for the synthesis of 6'-benzyloxycinchonine. One equivalent of tetrabutylammonium chloride was added to 6'-potassiumoxycinchonine dissolved in one liter of 1,2-dimethoxyethane followed by the addition of slightly less than one equivalent of allyl bromide. After stirring the mixture for 12 hours, the desired product was isolated according to the procedure described for the isolation of the 6'-benzyloxyderivative. The allyloxycinchonine was characterized by mass spectroscopy.

Example 4

Benzoylcupreidine (6'-Benzoylcinchonine)

Cupreidine (1.5 g) was dissolved in an aqueous solution containing one equivalent of potassium hydroxide. One equivalent of benzoyl chloride dissolved in several ml of monoglyme was added dropwise to the above solution which was rapidly stirred. After stirring for 30 minutes, the reaction mixture was extracted with 3 equal volumes of chloroform. The combined chloroform extract was washed with 5% NaOH solution followed by a like amount of water. The washed chloroform extract was dried over anhydrous sodium sulfate and evaporated to dryness. The solid residue was suspended in a small volume of benzene and filtered to yield 6'-benzoyloxycinchonine.

Example 5

Isovalerylcupreidine (6'-Isovaleryloxycinchonine)

This compound was prepared by an identical procedure as set forth in Example 4 for the synthesis of 6'-benzoyloxycinchonine.

Example 6

Cinnamoylcupreidine (6'-Cinnamoyloxycinchonine)

This compound was prepared by an identical procedure as set forth in Example 4 for the synthesis of 6'-benzoylcinchonine.

Example 7

Acetylcupreidine (6'-Acetylcinchonine)

This derivative was prepared by an identical procedure as set forth in Example 4 for the synthesis of 6'-benzoyloxycinchonine except that acetic anhydride was used.

A dosage in the same range as that previously set forth for cupreidine was utilized with mice for the compounds 6-benzylcinchonine and 6'-allylcinchonine. Aconitine was used to induce arrhythmia and a saline solution was used with the control group. The results are summarized below.

TABLE III

| | Saline | 6-Benzylcinchonine | 6'-Allylcinchonine |
|---|---|---|---|
| Onset of Arrhythmia (time in seconds) | 160. ± 5 | 195. ± 8 | 215. ± 9 |
| Onset of Ventricular Tachycardia (time in seconds) | 186. ± 6 | 217. ± 6 | 261. ± 11 |

Dosage levels, carriers and treatment schedules for the alternative compounds set forth above are comparable to the techniques discussed above for cupreidine.

A particularly useful group of compounds for accomplishing the objectives of the invention in the group consisting of the benzoyl, isovaleryl, cinnamoyl and acetyl derivatives of cupreidine as set forth in Examples 4, 5, 6 and 7 above. These compounds are all useful as antianhythmic agents at the dosages indicated.

We claim:
1. A compound of the formula:

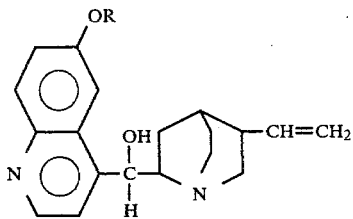
wherein R is benzoyl, isovaleryl, cinnamoyl or acetyl.
2. A method of treating arrhythmia comprising: administering to the subject an effective dose of a compound selected from the group comprising:
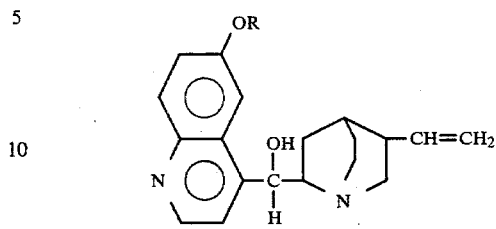
where R is benzoyl, isovaleryl, cinnamoyl or acetyl.
* * * * *